United States Patent [19]
Li

[11] Patent Number: 6,093,808
[45] Date of Patent: Jul. 25, 2000

[54] IκBEGFP CONSTRUCTS, CELL LINES AND METHODS OF USE

[75] Inventor: Xianqiang Li, Palo Alto, Calif.

[73] Assignee: Clontech Laboratories, Inc., Palo Alto, Calif.

[21] Appl. No.: 09/354,183

[22] Filed: Jul. 16, 1999

Related U.S. Application Data

[62] Division of application No. 09/062,070, Apr. 17, 1998.
[51] Int. Cl.⁷ .............................. C07H 21/04; C07K 1/00; C12Q 1/68; C12N 1/00; C12N 5/00
[52] U.S. Cl. ........................ 536/23.4; 536/23.4; 536/23.5; 530/350; 435/6; 435/325; 435/243; 435/320.1
[58] Field of Search ................................ 435/6, 325, 243, 435/320.1, 23.4; 536/23.5; 530/350

[56] References Cited

U.S. PATENT DOCUMENTS 5,597,898   1/1997   Ghosh et al. ............................ 530/350

OTHER PUBLICATIONS

Zolotukhin et al; A "Humanized" Green Fluorescent–Protein cDNA Adapted for high level expression in mammalian cells Journal of Virology 70; 4646–4654, Jul. 1996.

*Primary Examiner*—Nita Minnifield
*Assistant Examiner*—Padma Baskar
*Attorney, Agent, or Firm*—Benjamin Aaron Adler

[57] ABSTRACT

The present invention provides fusion protein comprising IκB and green fluorescent protein. Also provided is DNA encoding this protein and vector expressing such DNA and various methods of using a fusion protein comprising IκB and green fluorescent protein.

5 Claims, 10 Drawing Sheets

IκBEGFP CONSTRUCTS, CELL LINES AND METHODS OF USE

This is a divisional application of U.S. Ser. No. 09/062,070 filed on Apr. 17, 1998.

BACKGROUND OF THE INVENTION

1. Field of the Invention

The present invention relates generally to the fields of protein chemistry and biochemical assays and reagents. More specifically, the present invention relates to modified fluorescent proteins and to methods for their use.

2. Description of the Related Art

The Green Fluorescent Protein (GFP) from the jellyfish *Aequorea victoria* has been widely used as a reporter in the determination of gene expression and protein localization (1–4). GFP cDNA can be expressed in various cells or organisms with an easily detected fluorescence in the absence of any substrate or cofactor (5).

GFP is a 27-kDa, single-chain polypeptide of 238 amino acids (6). A key sequence of Ser-Tyr-Gly at amino acids 65 to 67 near the N terminus functions as the GFP fluorophore (7). These three amino acids undergo spontaneous oxidation to form a cyclized chromophore responsible for the fluorescence of GFP (8). Enhanced GFP (EGFP) is a mutant of GFP with a 35-fold increase in fluorescence (9–1 1). This variant has mutations of Ser to Thr at amino acid 65 and Phe to Leu at position 64, and is encoded by a gene with optimized human codons (10).

Because of its easily detectable green fluorescence, green fluorescent protein from the jellyfish *Aequorea victoria* has been used widely to study gene expression and protein localization. GFP fluorescence does not require a substrate or cofactor; hence, it is possible to use this reporter in numerous species and in a wide variety of cells. GFP is a very stable protein, and can accumulate; thus, GFP is often toxic to mammalian cells.

Recently, crystallographic structures of wild-type GFP and the mutant GFP S65T reveal that the GFP tertiary structure resembles a barrel (Ormo et al. (1996) *Science* 273: 1392–1395; Yang, F., Moss, L. G., and Phillips, G. N., Jr. (1996) *Nature Biotech* 14: 1246–1251). The barrel consists of beta sheets in a compact antiparallel structure. In the center of the barrel, an alpha helix containing the chromophore is shielded by the barrel. The compact structure makes GFP very stable under diverse and/or harsh conditions, such as protease treatment.

A great deal of research is being performed currently to improve the properties of GFP and to produce GFP reagents useful for a variety of research purposes. New versions of GFP have been developed via mutation, including a "humanized" GFP DNA, the protein product of which enjoys increased synthesis and improved folding in mammalian cells (see Cormack, B. P., Valdivia, R. H., and Falkow, S. (1996) *Gene* 173, 33–38; Haas, J., Park., E. C., and Seed, B. (1996) Current Biology 6, 315–324; and Yang, T. T., Cheng, L., Kain, S. R. (1996) *Nucleic Acids Research* 24, 4592–4593). One such humanized protein is "enhanced green fluorescent protein" (EGFP). Other mutations to GFP have resulted in blue- and red-fluorescent light emitting versions.

Cells are capable of responding to various stimuli by activating or repressing the expression of particular genes whose products exert a wide range of effects on biological processes. Such stimuli include heat shock, steroid hormone, growth factors, cytokines, etc. The process of gene transcription itself is the major point for regulation, although gene expression can be regulated at the post-transcriptional level. The external signals or stimuli may affect gene expression via regulation of transcriptional factors in a process called signal transduction. External signals exert influence by, for example, inducing conformational changes in these factors, modifying them chemically, or directing formation of ligand/protein complexes. The dissection of signal transduction pathways provide important information for the drug discovery and design.

A number of important signal transduction pathways require the activation of transcription factor NF-κB. Compounds affecting NF-κB activation include tumor necrosis factor α (TNFα), interleukin 1β (IL-1), liposaccharide (LPS), and phorbel ester (PMA). The activation of NF-κB leads to induction of a large array of genes whose products contribute diverse important biological processes, such as cell growth, apoptosis, inflammation, and immune responses. NFκB is the prototype of a family of dimeric transcription factors. It consists of p50(NFkB1), p52 (NFkB2), RelA(p65), RelB, c-Rel. The Rel/NFkB family of proteins share an approxomately 300-amino acid Rel region that binds to DNA, interacts with each other, and binds its inhibitor, IκB. There are at least six species IκB proteins that are identified to associate with NF-κB/Rel proteins. All IκB proteins have 5–7 ankyrin repeat domains, each with a length of about 30 amino acids, that interact with the NFκB Rel region.

The mechanism of NFκB activation has been well documented. NFκB is present in an inactive form in the cytoplasm where it is bound to IκB. Cellular activation in response to a variety of inducers leads to the rapid release of NFκB from IκB. This activation is independent on protein synthesis. In response to diverse stimuli, an intracellular cascade of protein kinase activity is triggered, and IκB is phosphorylated at two serines (Ser 32 and Ser 36) specifically and degraded rapidly by 26S proteasome. Uncomplexed NFκB rapidly translocates to the nucleus where transcriptional activation of gene expression occurs within minutes.

The search for agonists or antagonists that can activate or inhibit NFκB are major drug targets for pharmaceutical companies. Two very common methods used for studying the activation of gene expression are the in vitro gel shift assay or assays involving in vivo transcriptional induction of a reporter. Because the mechanism of NFκB activation is well defined, a number of assays based on the activation pathway have been designed and used to monitor NFκB-induced gene expression. The assays include measuring phosphorylation of IκB, degradation of IκB, and ubiquitination of IκB. These assays are often used in the research labs; however, for large scale drug screening, the assays are either time consuming or tedious.

The prior art is deficient in an methods and research tools for easy, high throughput assays for measuring degradation of IκB. The present invention satisfies this long-standing need in the art.

SUMMARY OF THE INVENTION

The fusion protein consisting of IκB and humanized green fluorescent protein of the present invention provides a research tool for measuring degradation of IκB in a straight-forward manner. Cells expressing this fusion protein maintain GFP-induced fluoresce as long as the degradation of IκB has not been triggered. However, as soon as external factors induce phosphorylation of IκB triggering IκB degradation, the IκB portion of the fusion protein is degraded, and the GFP portion of the fusion ceases to fluoresce. Thus, the IκB-EGFP fusion protein provides a tool for a direct, visual assay of IκB degradation. Such an assay is applicable in high throughput formats.

The present invention provides an IκBEGFP fusion protein wherein fluorescence of the fusion protein is dependent upon the IκB portion of the fusion protein being intact. In one embodiment, there is provided a fusion protein comprising an IκB fused to a GFP.

In yet another aspect of the invention, there is provided an isolated DNA molecule encoding an IκB/GFP fusion protein wherein fluorescence of the fusion protein is dependent upon the IκB portion of the fusion protein being intact. In one embodiment of this aspect of the invention, the isolated DNA molecule encoding the GFP portion of the fusion protein is humanized. Further, the present invention provides a vector capable of expressing the isolated DNA molecule encoding the IκB/GFP fusion protein wherein fluorescence of the fusion protein is dependent upon the IκB portion of the fusion protein being intact. In one embodiment of the vector, the vector contains an inducible promoter. In another aspect of the invention, there is provided a mammalian cell stably-transfected with a DNA expressing the IκB/GFP fusion protein of the present invention.

In yet another aspect of the invention, there are provided assays for determining agonists or antagonists that activate or inhibit NFκB via measuring degradation of IκB. In one embodiment of this aspect, there is provided a method of determining activation of NFκB by a compound of interest, comprising the steps of: introducing into a cell a vector expressing an isolated DNA molecule encoding an IκB-GFP fusion protein; contacting said cell with said compound of interest; measuring the amount of GFP-induced fluorescence, wherein a decrease in GFP-induced fluorescence by said compound indicates that said compound activates NFκB. Generally, the decrease in GFP-induced fluorescence is directly proportional to the degradation of IκB.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
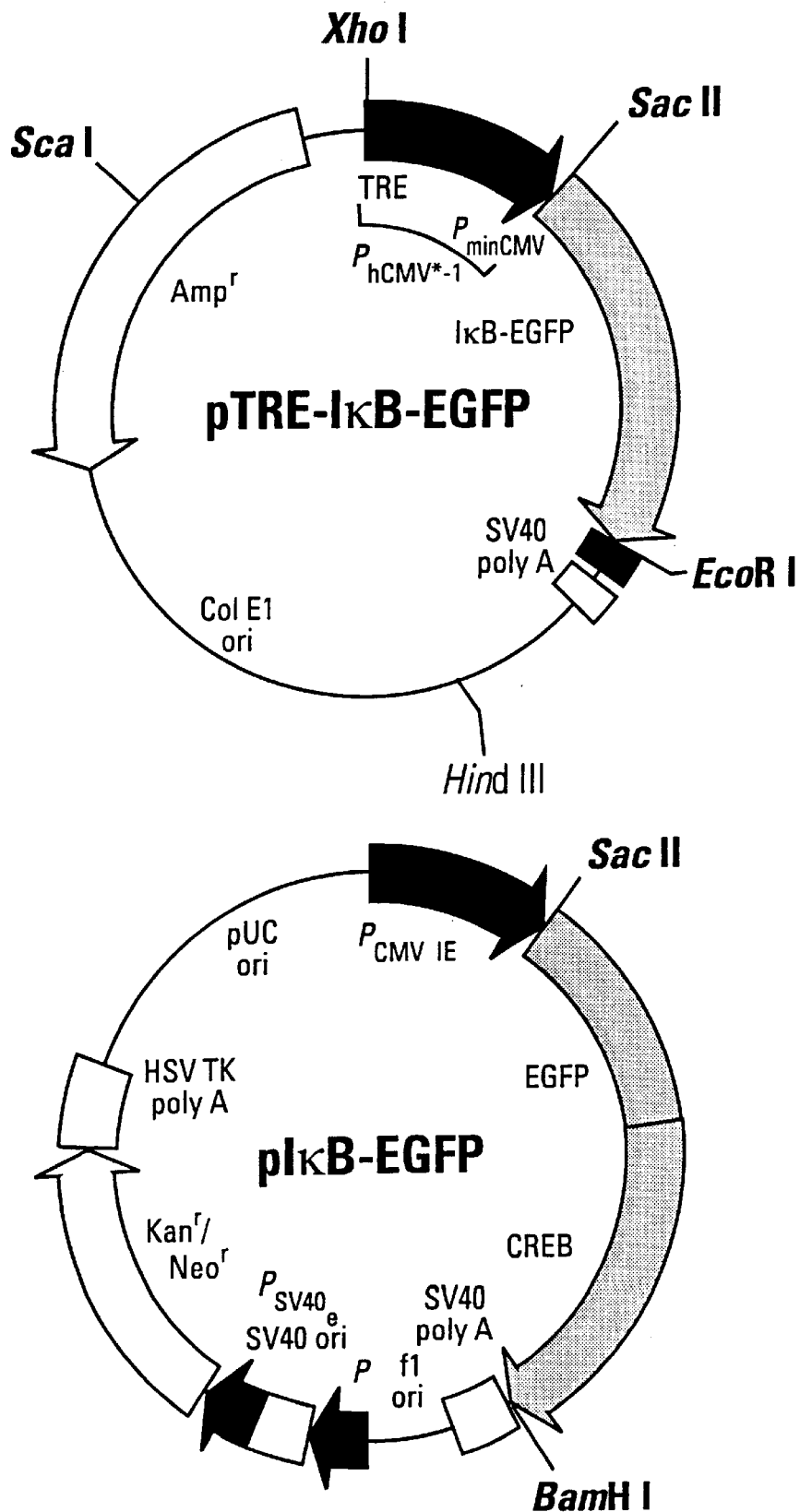
FIG. 1 shows a is a schematic of a vector which expresses one embodiment of the IκB/GFP fusion protein of the present invention.
Figure 2:
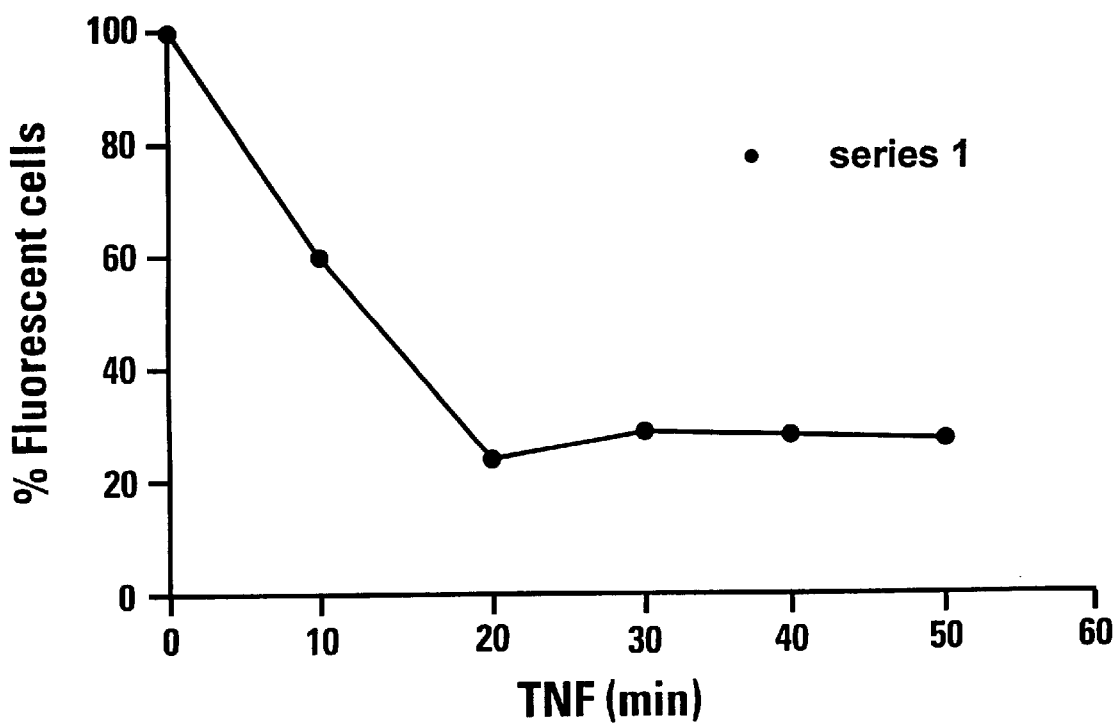
FIG. 2 illustrates the decrease in fluorescence after treatment with TNF-alpha in Hela tet-off cells stably transfected with a vector which expresses an IκB/GFP fusion protein. Cells were treated with TNF-alpha and examined at 0, 10, 20 and 30 minutes. Fluorescence was observed in cells at 0 and 10 minutes, but not at or 30 minutes.
Figure 3A:
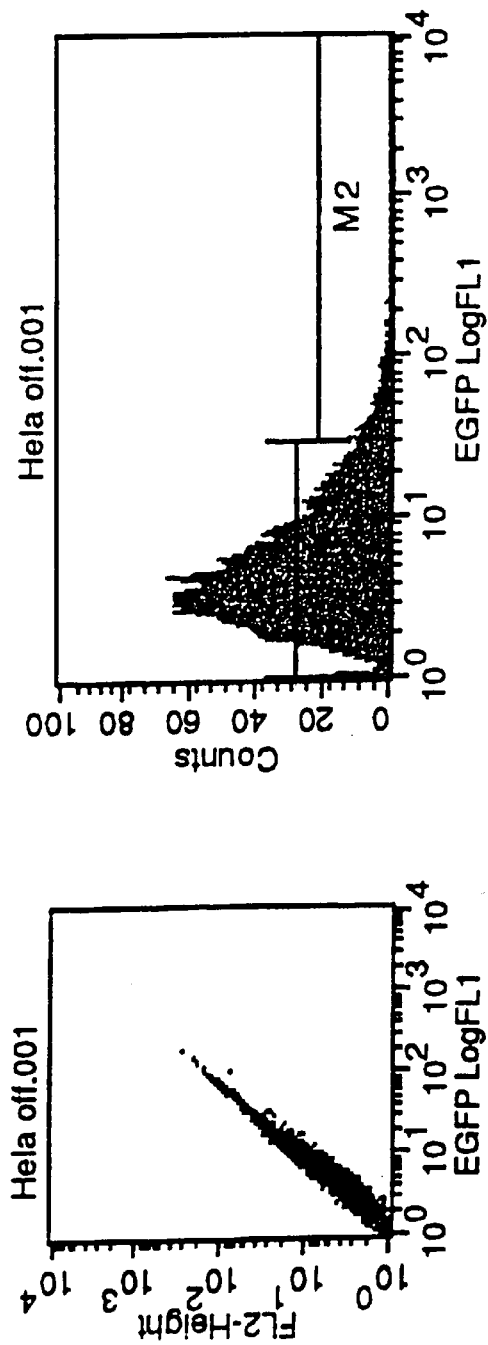
FIG. 3 shows the results flow cytometric analysis of Hela tet-off cells stably transfected with a vector which expresses an IκB/GFP fusion protein. Again, cells were treated with TNF-alpha and aliquots were tested for fluorescence at the indicated time points. Results indicate that the half life of the IκBEGFP fusion protein is approximately 15 minutes.
Figure 3B:
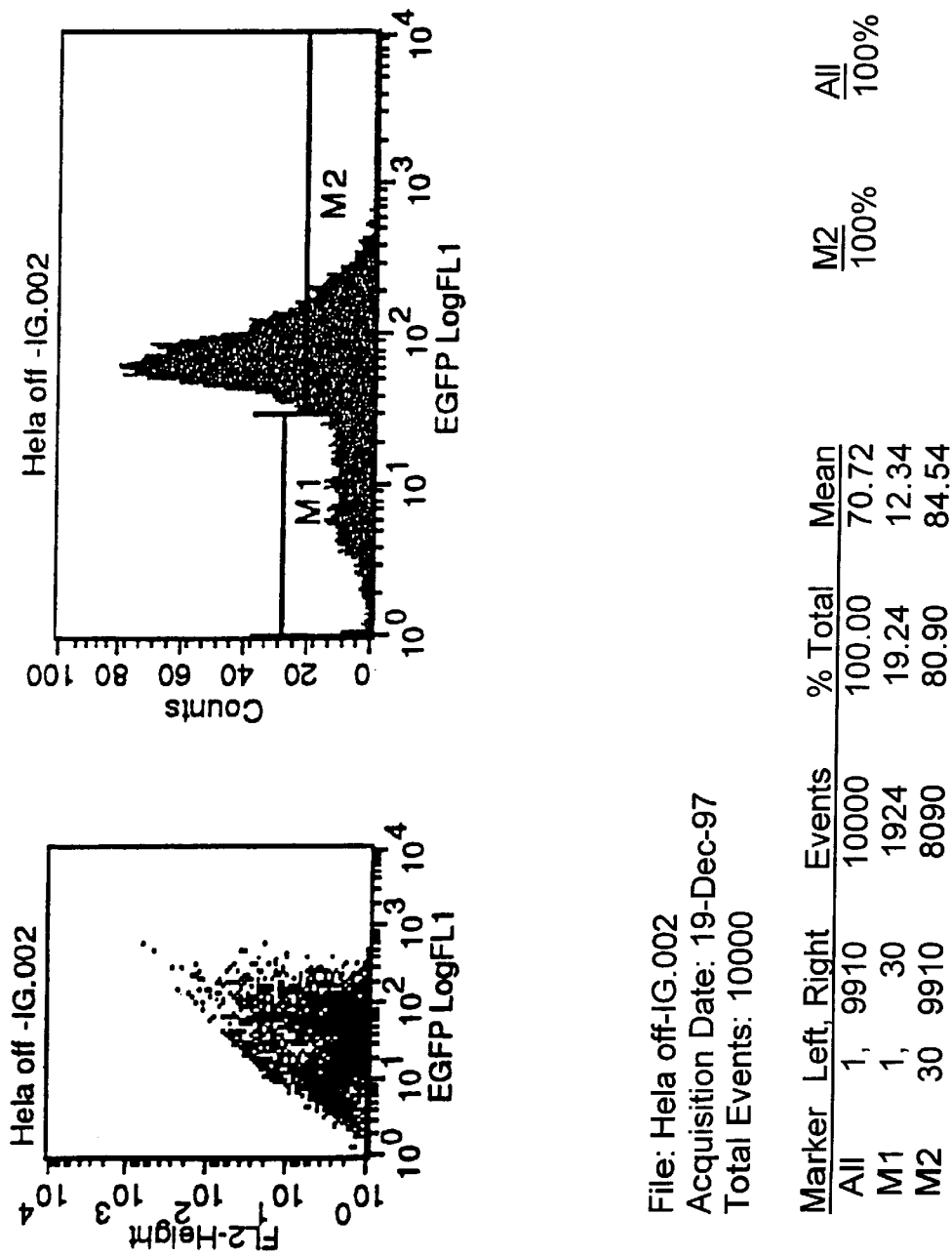
Figure 3C:
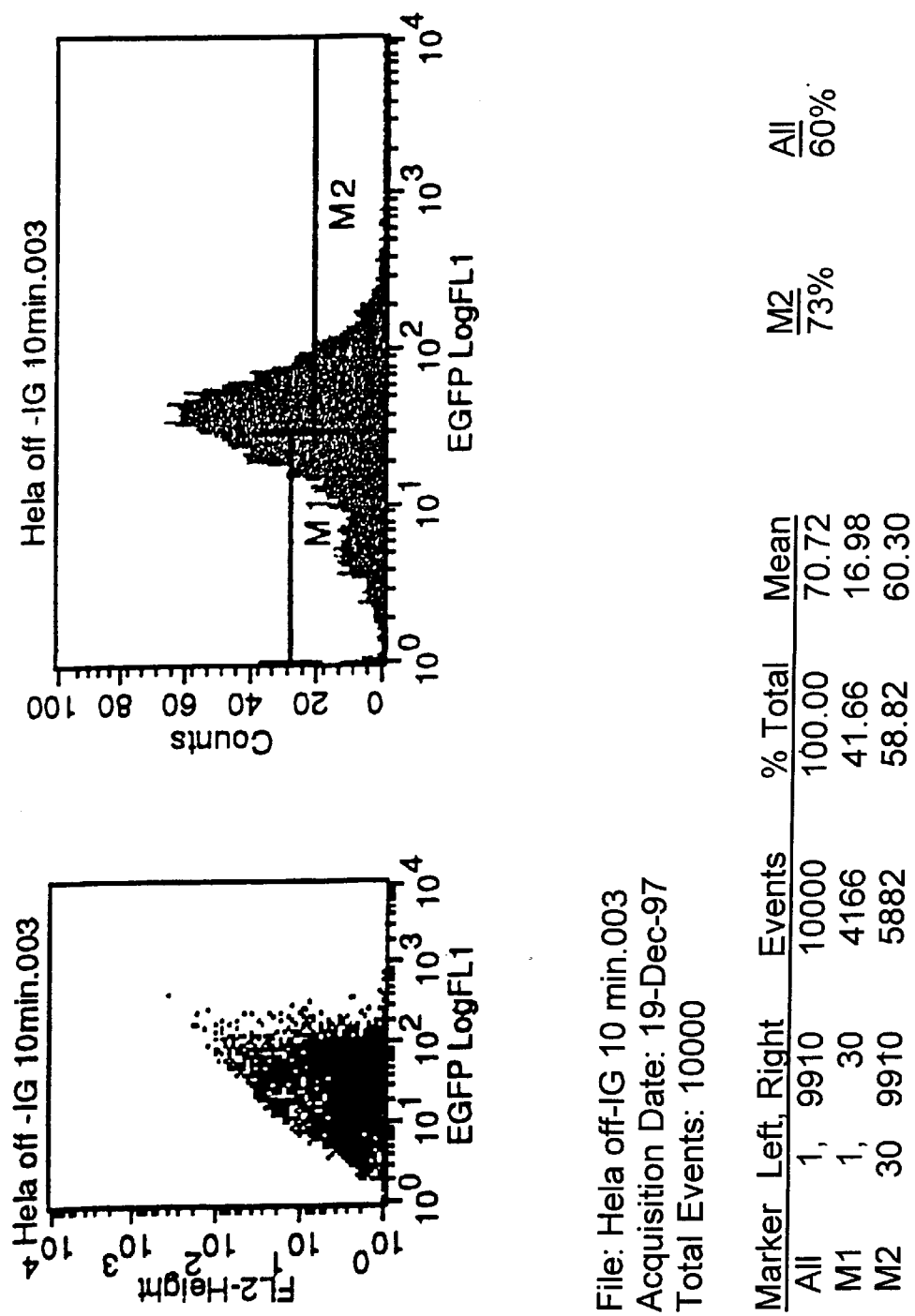
Figure 3D:
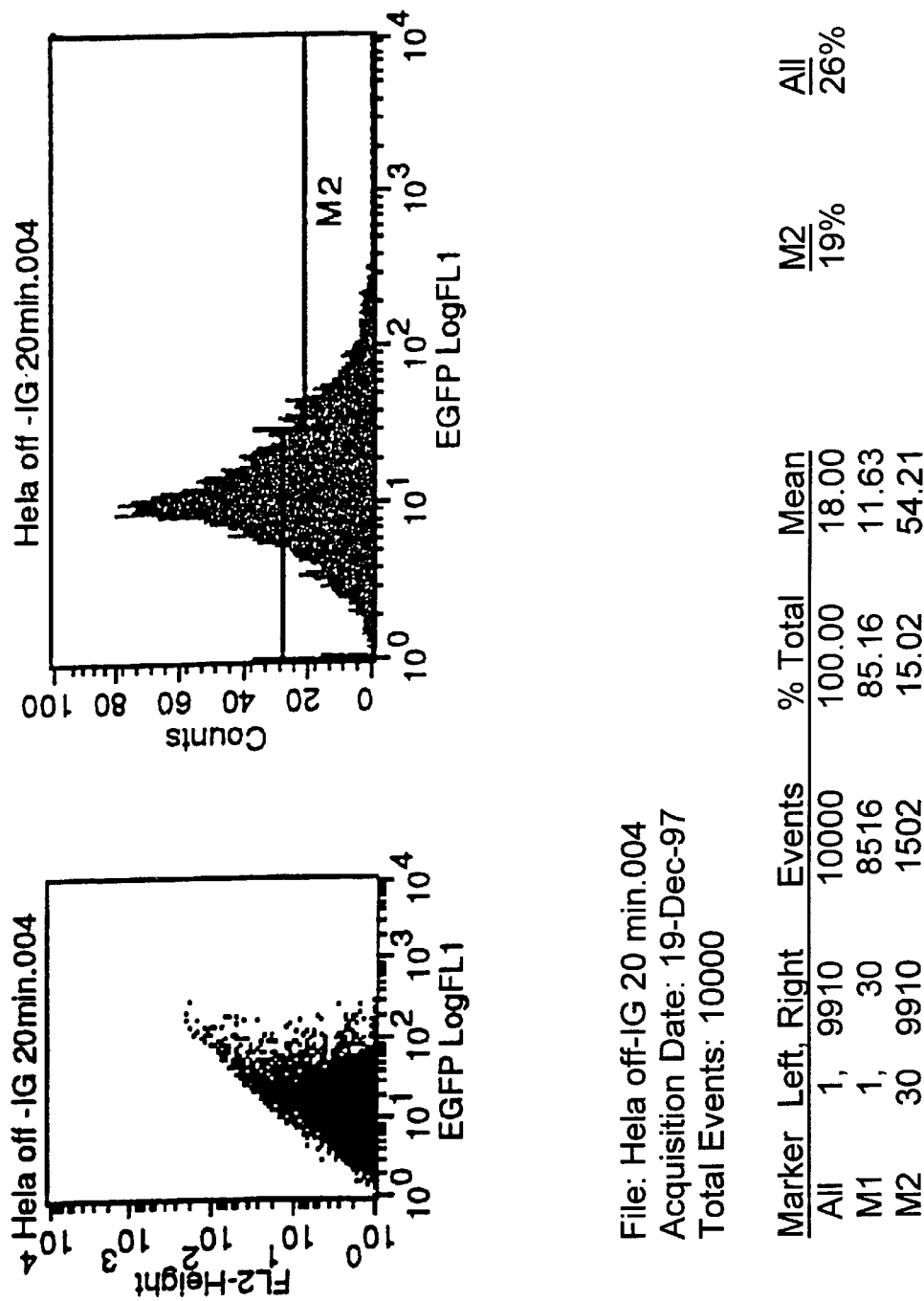
Figure 3E:
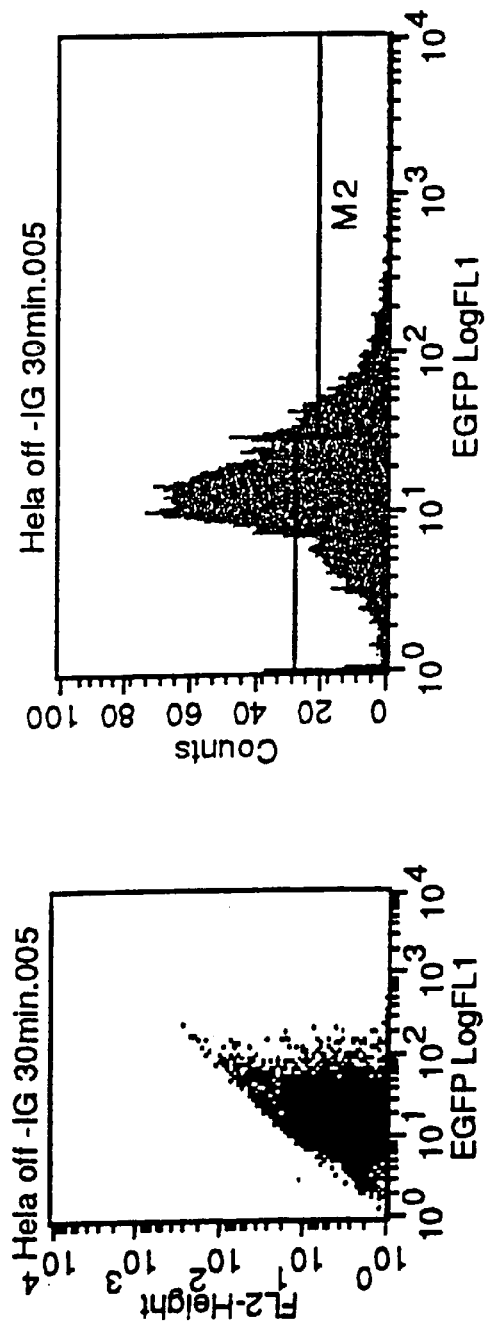
Figure 3F:
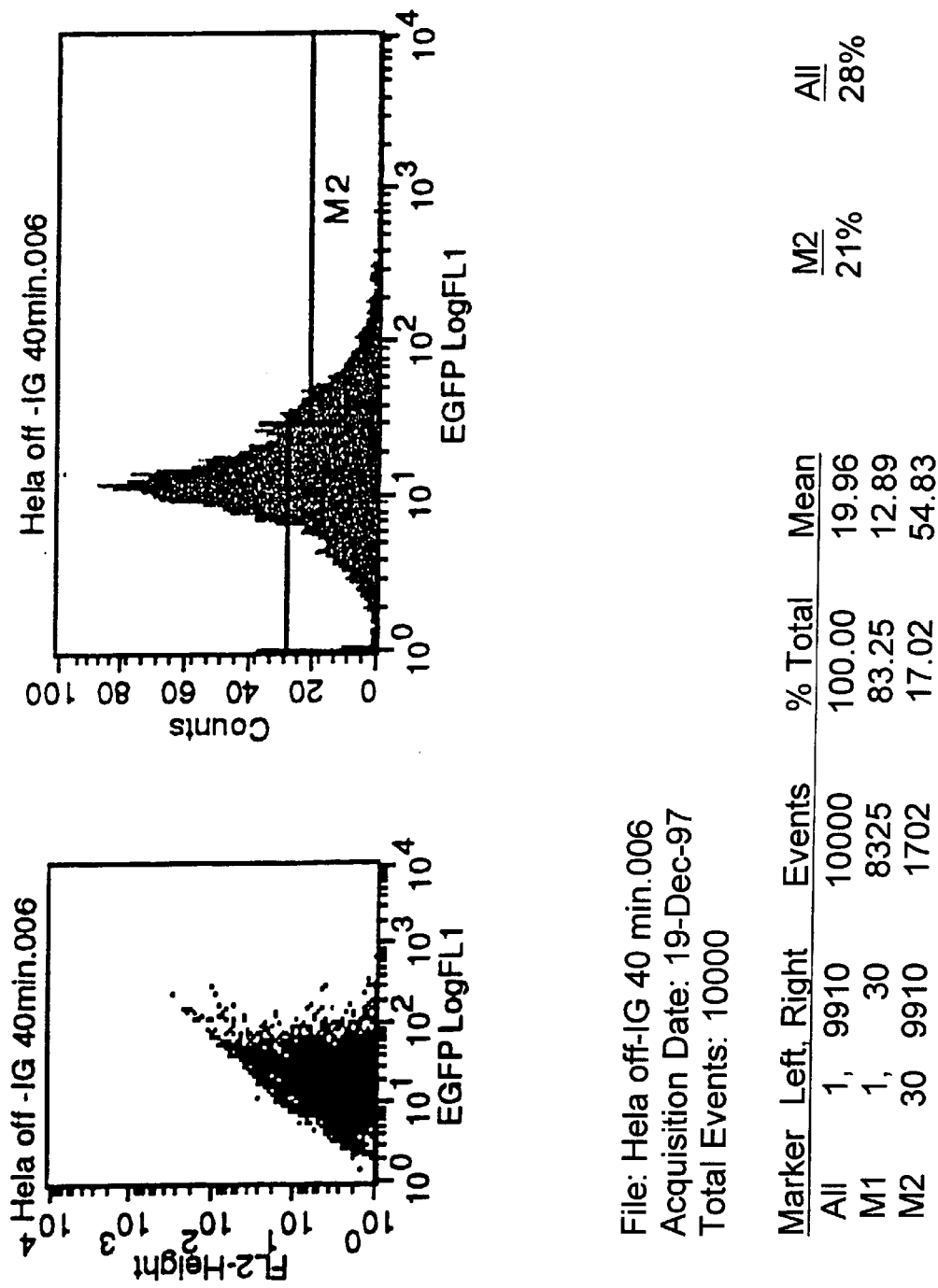
Figure 3G:
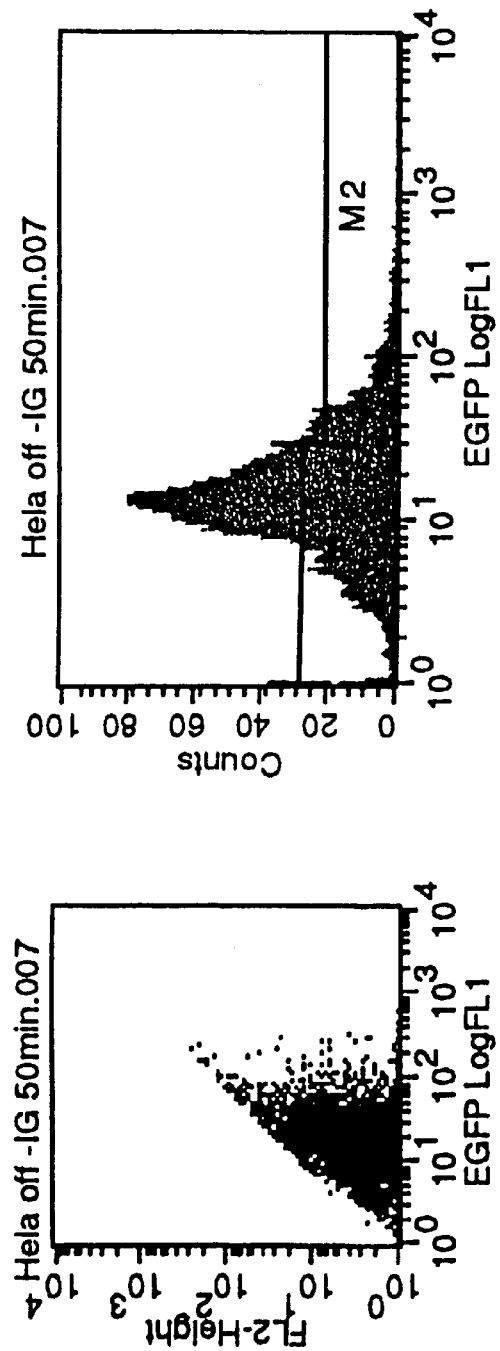
Figure 4:
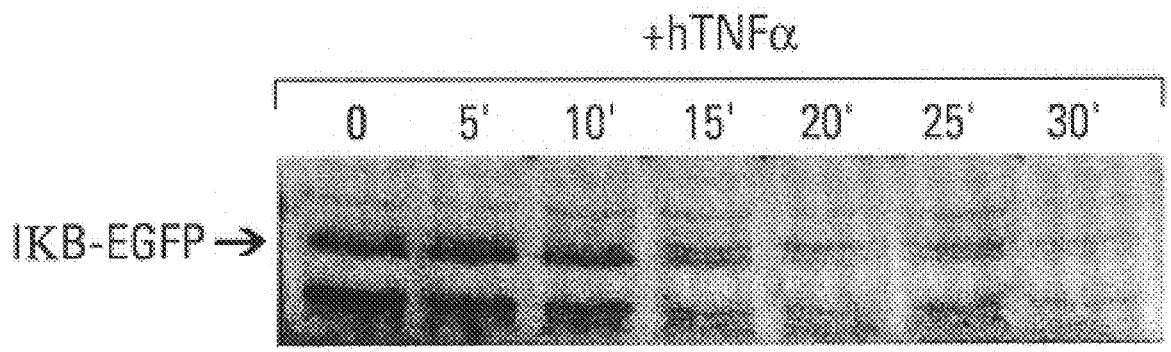
FIG. 4 is a western blot of protein extracts from Hela tet-off cells stably transfected with a vector which expresses an IκBlGFP fusion protein, using a monoclonal antibody against GFP. The size of the fusion protein is 65 kDa, as expected. Presence of the fusion protein declined upon treatment with TNF-alpha.

The present invention provides a fusion protein consisting of IκB/GFP and assays to monitor NFκB activation by determining cellular fluorescence using this fusion protein. As a result of expressing the IκB/GFP fusion protein, fluorescence in these cells corresponds directly with existence of intact IκB, which, in turn, corresponds directly to the state of NFκB activation. Upon exposure of these cells to various stimuli in which degradation of IκB is induced, degradation of the GFP portion of the fusion protein is triggered as well. Degradation of the fusion protein can be measured directly by determining the change in fluorescence of transfected cells.

As used herein, the term "GFP" refers to the basic green fluorescent protein from *Aequorea Victoria*, including prior art versions of GFP engineered to provide greater fluorescence or fluoresce in different colors. The sequence of A. Victoria GFP has been disclosed in Prasher D. C. et al (1992) *Gene* 111:229–33.

As used herein, the term "EGFP" refers to GFP which has been "humanized", as reported in Kain et al. (1995) *Biotechniques* 19(4):650–55. "Humanized" refers to changes made to the GFP nucleic acid sequence to optimize the codons for expression of the protein in human cells.

As used herein, the term "half life" refers to the period of time in which half of the fluorescent signal from a fluorescent protein expressed in cells disappears and half remains.

As used herein, the term "humanized" refers to engineering a DNA sequence coding for a protein such that the codons are optimized for translation in higher eukaryotes.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

Transcriptional and translational control sequences are DNA regulatory sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. Generally, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "promoter" refers to any nucleic acid sequence whose regulation affects expression and production of the green fluorescent protein of the present invention.

Transcriptional and translational control sequences are NA regulatory sequences, such as promoters, enhancers, polyadenylation signals, terminators, and the like, which provide for the expression of a coding sequence in a host cell.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are shown in the following Table of Correspondence:

| Y | Tyr | tyrosine |
|---|-----|----------|
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

All amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

The present invention discloses a fusion protein comprising IκB and green fluorescent protein. In one aspect, the protein is a wild type green fluorescent protein. In another aspect, the protein is a humanized green fluorescent protein. Preferably, the protein is an enhanced green fluorescent protein.

The present invention is also directed to an isolated DNA molecule encoding an IκB/GFP fusion protein. In addition, the present invention describes a vector capable of expressing this isolated DNA molecule. Further, the present invention is directed to a cell line transfected with this vector.

The present invention is also directed to a method of determining activation of NFκB by a compound of interest, comprising the steps of introducing into a cell a vector expressing an isolated DNA molecule encoding an IκB-GFP fusion protein; contacting said cell with said compound of interest; and measuring the amount of GFP-induced fluorescence, wherein a decrease in GFP-induced fluorescence by said compound indicates that said compound activates NFκB. The decrease in GFP-induced fluorescence is directly proportional to the degradation of IκB.

The following examples are given for the purpose of illustrating various embodiments of the invention and are not meant to limit the present invention in any fashion.

EXAMPLE 1
Generation of IkBα-EGFP Fusion Protein

The cDNAs encoding IkBα and EGFP were amplified with Pfu DNA polymerase. IkBα was amplified with primers that incorporated a SacII recognition sequence at the 5' end and a BamH I sequence at the 3' end. The stop codon of IkBα was deleted during PCR amplification in order to make an open reading frame with EGFP. EGFP was amplified with primers that incorporated a BamH I recognition sequence at the 5' end and an EcoRI sequence at the 3' end. The amplified PCR products were ligated at the BamH I site and the resulting fusion constructs (IkBα-EGFP) were cloned into Sacll and EcoRI sites of the pTRE expression vector for use in the Tetracycline (Tc)-regulated expression system (Gossen M., and Bujard H. (1992) *Proc. Natl. Acad. Sci. U.S.A.* 89, 5547–5551).

EXAMPLE 2
Establishment of a Hela Cell Line Expressing the Fusion Protein

To make stable cell lines, DNA constructs were co-transfected into Hela Tet-off cells with pTK-Hyg. Hela tet-off cells are Hela cells which were pre-transfected by a fusion protein of the tet-repressor and the herpes simplex virus VP16 (tTA). This pre-transfection allows expression of the gene on pTRE vector (Gossen and Bujard, ibid), which in turn initiates transcription by binding to a modified CMV promoter with tet-repressor binding elements. This binding can be blocked by tetracycline; hence, the expression can be controlled by tetracycline. The transfected cells were cultured in a medium containing hygromycin to select drug resistant cells. The drug-resistant colonies were then screened for green fluorescent clones under a fluorescence microscope. The fluorescent clones were selected and transferred.

EXAMPLE 3
Fluorescence Analysis

Cells were cultured on top of cover-slips to allow observation under a fluorescence microscope. After transfection, the cells were incubated at 37° C. for 24 hours on the cover-slips and then fixed with 4% paraformaldehyde for 30 minutes. The cover-slips were mounted on a glass slide for fluorescence examination with a Zeiss Axioskop Model 50 fluorescent microscope. To determine protein turnover, the cells were treated with TNF for varying times before paraformaldehyde fixation. The transfected cells were collected by EDTA treatment and the cell pellets resuspended in 0.5 ml of PBS. The cell suspensions were analyzed for fluorescence intensity using a FACS Calibur flow cytometer (Becton Dickson, Inc., San Jose, Calif.). EGFP was excited at 488 nm, and emission detected using a 510/20 bandpass filter.

For FACS analysis, the transfected cells were collected by EDTA treatment and the cell pellets were resuspended in 0.5 ml of PBS. The cell suspensions were then analyzed for fluorescence intensity by FACS Calibur (Becton Dickson, Inc., San Jose, Calif.). EGFP was excited at 488nm, and emission was detected using a 510/20 bandpass filter.

EXAMPLE 4
Western Blot Analysis

For western blot analysis, transfected control cells were collected in PBS and sonicated to prepare cell lysates. Proteins were separated by SDS-PAGE. The IkBα-EGFP fusion proteins were detected by a monoclonal antibody against GFP after the proteins were transferred onto a membrane. The detection was visualized with a chemiluminescent detection kit (CLONTECH).

EXAMPLE 5
Characterization of IkBαEGFP

A stable cell line expressing the IkBαEGFP fusion protein was established by co-transfecting the pTRE-IkBαEGFP construct with a pTK-hygromycin construct, selecting the resistant colonies, and screening for fluorescence under a fluorescent microscope. Two clones were selected, and because each clone is derived from a single colony, every single cell fluoresces. This makes the observation and detection much easier.

To examine more carefully the regulation of the fluorescence, cells were treated with TNF for 0, 20, 40, 60 and 80 minutes and aliquots of cells were monitored for fluorescence intensity at various time points. Fluorescence declined rapidly after the treatment, even after 20 minutes. Thus, time for TNF treatment was shortened and the experiments were repeated. Cells were treated for 0, 10, 20 and 30 minutes with TNF, and fluorescence was observed in cells that were treated for 0 or 10 minutes, but not cells treated for 20 and 30 minutes. These results suggest that the half life of the fluorescence of the fusion protein is about 10 to 20 minutes.

Next, flow cytometry was used to analyze quantitatively the half life of the fluorescence. In this study, cells were treated with TNF for 0, 10, 20, 30, 40, and 50 minutes and collected for analysis. Fluorescence declined to a basal level after 20 minute treatment, agreeing with the observations obtained with the fluorescent microscope.

To more accurately determine fluorescence half life of the fusion protein, cells were treated with TNF for 0, 5, 10, 15 and 20 minutes. Results indicated that the half life of the fluorescence of the fusion protein is 15 minutes—very close to the half life of IkB protein that was determined in TNF treated Hela cells. The EGFP tag neither changes TNF-mediated regulation of IκB nor its half life. Therefore, the fusion protein IkBαEGFP can be used to monitor IκB degradation.

To examine if TNF-mediated IG degradation is cell growth-dependent or not, the cells of the IG clone was cultured in regular serum medium overnight. The cells were washed and medium was replaced with serum free medium. The growth-arrested cells were then treated with TNF for 30 minutes. The fluorescence of the growth-arrested cells did not change dramatically compared to the growing cells. The fluorescence was still sensitive to the TNF treatment, suggesting that TNF-mediated IKB degradation is independent of cell growth.

EXAMPLE 6
Further Characterization of IkBαEGFP

To confirm that the fluorescence change represents the change of protein level and not the influence of an external factor that might effect fluorescence, protein change was measured by Western blot analysis with a monoclonal antibody against recombinant GFP. The cells were treated with TNF-alpha for 0, 5, 10, 15, and 20 minutes. The molecular size of the IkBαEGFP fusion protein is about 65 kDa, as was predicted. The presence of the fusion protein declined with the increase of time of TNF treatment. After 10 minutes of treatment, more than half amount of the fusion protein disappeared, confirming the results obtained mearuing fluorescence—that the half life of the fusion protein is less than 15 minutes.

The following references were cited herein:
1. Chalfie, M., Euskirchen, G., Ward, W. W., and Prasher, D. C. (1994) *Science* 263, 802–805.
2. Marshall, J., Molloy, R., Moss, G. W., Howe, J. R. and Hughes, T. E. (1995) *Neuron* 14, 211–215.
3. Chalfie, M. (1995) Photochemistry and Photobiology 60, 651–656.
4. Cubitt, A. B., Heim, R., Adams, S. R., Boyd, A. E., Gross, L. A., and Tsien R. Y. (1995) *Trends Biochem* 20, 448–455.
5. Heim, R., Prasher, D. C., Tsien, R. Y. (1994) *Proc. Natl. Acad. Sci.U.S.A.* 91, 12501–12504.
6. Inouge, S., and Tsuji, F. I. (1994) *FEBS Letters* 351, 211–214
7. Cormack, B. P., Valdivia, R. H., and Falkow, S. (1996) *Gene* 173, 33–38.
8. Haas, J., Park., E. C., and Seed, B. (1996) *Current Biology* 6, 315–324.
9. Yang, T. T., Cheng, L., Kain, S. R. (1996) *Nucleic Acids Research* 24, 4592–4593.
10. Ormo, M., Cubitt, A. B., Kallio, K., Gross, L. A., Tsien, R. Y., Remington S. J. (1996) *Science* 273, 1392–1395.
11. Yang, F., Moss, L. G., and Phillips, G. N., Jr. (1996) *Nature Biotechnology* 14, 1246–1251.
12. Prasher, D. C. Eckenrode, V. K. Ward, W. W., Prendergast, F. G. and Cormier, M. J. (1992) *Gene* 111, 229–233.
14. Lybarger, L., Dempsey, D., Franek, K. J., Chervenak, R. (1996) *Cytometry* 25, 211–220.
15. Rogers, S. R., Wells, R., and Rechsteiner, M. (1986) *Science* 234, 364–3 68.
16. Ghoda, L., Van Daalen Wetters, T., Macrase, M., Ascherman D., and Coffino, P. (1989) *Science* 243, 1493–1495.
17. Papavassiliou, A. G., Treier, M., Chavrier, C., and Bohmann, D. (1992) *Science* 258, 1941–1944.
18. Scheffner, M., Werness, B. A., Huibregtse, J. M., Levine, A. J., and Howley, P. M. (1990) *Cell* 63, 1129–1136.
19. Li, X., and Coffino, P. (1992) *Mol. Cell. Biol.* 12, 3556–3562. 20. Goldberg, A. L., and Rock, K. L., (1992) *Nature* 357, 375–379.
21. Gottesman, S., and Maurizi, M. R. (1992) *Microbiol. Rev.* 56, 592–621
22. Hershko, A., and Ciechanover, A. (1992) *Annu. Rev. Biochem.* 61, 761–807.
23. Rechsteiner, M., Hoffman, L., and Dubiel, W. (1993) *J. Biol. Chem.* 268, 6065–6068.
24. Bercovich, Z., Rosenberg-Hasson, Y., Ciechanover, A., and Kahana, C., (1989) *J. Biol. Chem.* 264, 15949–15952.
25. Rosenberg-Hasson, Y., Bercovich, Z., Ciechanover, A., and Kahana, C. (1989) *Eur. J. Biochem.* 185, 469–474.
26. Murakami, Y., Matsufuji, S., Kameji, T., Hayashi, S., Igarashi, K., Tamura, T., Tanaka, K., Ichihara, A. (1992) *Nature* 360, 597–599.
27. Ghoda, L., Phillips, M. A., Bass, K. E., Wang, C. C., and Coffino, P. (1990) *J. Biol. Chem.* 265, 11823–11826.
28. Phillips, M. A., Coffino, P., and Wang, C. C. (1987) *J. Biol. Chem.* 262, 8721–8727.
29. Gossen M., and Bujard H. (1992) *Proc. Natl. Acad. Sci. U.S.A.* 89, 5547–5551.
30. Ghoda, L., Sidney, D., Macrae, M., and Coffino, P. (1992) *Mol. Cell. Biol.* 12, 2178–2185.
31. Li, X., and Coffino, P. (1993) *Mol. Cell. Biol.* 13, 2377–2383.
32. Loetscher, P., Pratt, G., Rechsteiner, M. (1991) *J. Biol. Chem.* 266, 11213–11220.
33. Li, X., Stebbins, B., Hoffman, L., Pratt, G., Rechsteiner, M., and Coffino, P. (1996) *J. Biol. Chem.* 271, 4441–4446.
34. Li, X., and Coffino, P. (1996) *J. Biol. Chem.* 271, 4447–4451.
35. Li, X., and Coffino, P. (1994) *Mol. Cell. Biol.* 14, 87–92.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA molecule, encoding an IκB/GFP fusion protein for measuring degradation of IκB in vitro, comprising IκB and green fluorescent protein.

2. A vector capable of expressing the isolated DNA molecule of claim 1.

3. A cell line transfected with the vector of claim 2.

4. A method of determining activation of NFκB by a compound of interest, comprising the steps of:

introducing into a cell a vector expressing an isolated DNA molecule encoding an IκB-GFP fusion protein of claim 1;

contacting said cell with said compound of interest;

measuring an amount of GFP-induced fluorescence, wherein a decrease in GFP-induced fluorescence by said compound indicates that said compound activates NFκB.

5. The method of claim 4, wherein a decrease in GFP-induced fluorescence is directly proportional to the degradation of IκB.

* * * * *